US010363038B2

(12) United States Patent
Marczyk (10) Patent No.: US 10,363,038 B2
(45) Date of Patent: *Jul. 30, 2019

(54) SURGICAL STAPLING APPARATUS WITH POWERED RETRACTION (71) Applicant: Covidien LP, Mansfield, MA (US)

(72) Inventor: Stanislaw Marczyk, Stratford, CT (US)

(73) Assignee: Coviden LP, Mansfield, MA (US)

( * ) Notice: Subject to any disclaimer, the term of this patent is extended or adjusted under 35 U.S.C. 154(b) by 394 days.

This patent is subject to a terminal disclaimer.

(21) Appl. No.: 15/185,557

(22) Filed: Jun. 17, 2016

(65) Prior Publication Data

US 2016/0287256 A1 Oct. 6, 2016

Related U.S. Application Data (63) Continuation of application No. 13/913,538, filed on Jun. 10, 2013, now Pat. No. 9,370,360, which is a
(Continued)

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC ................ A61B 17/105; A61B 17/068; A61B 17/07207; A61B 2017/00398; A61B 2017/2923; A61B 2017/2943
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

EP 1520521 A1 4/2005
EP 1769755 A2 4/2007
(Continued)

OTHER PUBLICATIONS

European Search Report for EP 08251204.7-2310 date of completion is Jun. 25, 2010 (3 pages).
(Continued)

*Primary Examiner* — Michelle Lopez (57) ABSTRACT

A surgical stapling apparatus comprises a handle assembly, an actuation shaft having a connector, and a retraction mechanism positioned within the handle assembly. The retraction mechanism includes a motor coupled to a transmission shaft, a first gear rotatably mounted on the transmission shaft, the first gear configured to engage a second gear, a clutch operatively attached to the second gear, a main shaft rotatably connected to the clutch, and a pulley coupled to the main shaft, the pulley being operatively attached to the connector. The connector and the pulley may be attached via a cable. The retraction mechanism may include a spring motor for maintaining the cable in tension. The spring motor may have a spring element wrapped around and interconnecting at least two arbors.

17 Claims, 8 Drawing Sheets

Related U.S. Application Data continuation of application No. 13/489,517, filed on Jun. 6, 2012, now Pat. No. 8,479,967, which is a continuation of application No. 13/196,126, filed on Aug. 2, 2011, now Pat. No. 8,210,412, which is a continuation of application No. 11/784,804, filed on Apr. 9, 2007, now Pat. No. 8,006,885.

(51) Int. Cl.
*A61B 17/068* (2006.01)
*A61B 17/00* (2006.01)
*A61B 17/29* (2006.01)

(52) U.S. Cl.
CPC .............. *A61B 2017/00398* (2013.01); *A61B 2017/2923* (2013.01); *A61B 2017/2943* (2013.01)

(58) Field of Classification Search
USPC ...................................................... 227/175.1
See application file for complete search history.

(56) References Cited

U.S. PATENT DOCUMENTS

| | | |
|---|---|---|
| 3,499,591 A | 3/1970 | Green |
| 4,429,695 A | 2/1984 | Green |
| 4,529,044 A | 7/1985 | Klueber et al. |
| 4,566,620 A | 1/1986 | Green et al. |
| 4,610,383 A | 9/1986 | Rothfuss et al. |
| 5,065,929 A | 11/1991 | Schulze et al. |
| 5,207,697 A | 5/1993 | Carusillo et al. |
| 5,307,976 A | 5/1994 | Olson et al. |
| 5,312,023 A | 5/1994 | Green et al. |
| 5,312,024 A | 5/1994 | Grant et al. |
| 5,318,221 A | 6/1994 | Green et al. |
| 5,326,013 A | 7/1994 | Green et al. |
| 5,332,142 A | 7/1994 | Robinson et al. |
| 5,467,911 A | 11/1995 | Tsuruta et al. |
| 5,482,100 A | 1/1996 | Kuhar |
| 5,601,224 A | 2/1997 | Bishop et al. |
| 5,632,433 A | 5/1997 | Grant et al. |
| 5,676,674 A | 10/1997 | Bolanos et al. |
| 5,680,981 A | 10/1997 | Mililli et al. |
| 5,779,130 A | 7/1998 | Alesi et al. |
| 5,865,361 A | 2/1999 | Milliman et al. |
| 5,954,259 A | 9/1999 | Viola et al. |
| 6,079,606 A | 6/2000 | Milliman et al. |
| 6,241,139 B1 | 6/2001 | Milliman et al. |
| 6,330,965 B1 | 12/2001 | Milliman et al. |
| 6,505,768 B2 | 1/2003 | Whitman |
| 6,669,073 B2 | 12/2003 | Milliman et al. |
| 6,698,643 B2 | 3/2004 | Whitman |
| 6,716,233 B1 | 4/2004 | Whitman |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 7,000,819 B2 | 2/2006 | Swayze et al. |
| 7,044,353 B2 | 5/2006 | Mastri et al. |
| 7,083,075 B2 | 8/2006 | Swayze et al. |
| 7,143,925 B2 | 12/2006 | Shelton, IV et al. |
| 7,143,926 B2 | 12/2006 | Shelton, IV et al. |
| 7,431,188 B1 | 10/2008 | Marczyk |
| 8,479,967 B2 * | 7/2013 | Marczyk .......... A61B 17/07207 227/175.1 |
| 9,370,360 B2 | 6/2016 | Marczyk |
| 2002/0025891 A1 | 2/2002 | Colosky et al. |
| 2003/0009441 A1 | 1/2003 | Holsten et al. |
| 2003/0105475 A1 | 6/2003 | Sancoff et al. |
| 2004/0232201 A1 | 11/2004 | Wenchell et al. |
| 2005/0067458 A1 | 3/2005 | Swayze et al. |
| 2005/0070958 A1 | 3/2005 | Swayze et al. |
| 2005/0178813 A1 | 8/2005 | Swayze et al. |
| 2006/0175375 A1 | 8/2006 | Shelton et al. |
| 2007/0175952 A1 | 8/2007 | Shelton et al. |
| 2007/0175953 A1 | 8/2007 | Shelton et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |

FOREIGN PATENT DOCUMENTS

| | | |
|---|---|---|
| EP | 1813205 A1 | 8/2007 |
| EP | 1872727 A1 | 1/2008 |
| EP | 1980214 A2 | 10/2008 |
| WO | 2006132992 A2 | 12/2006 |

OTHER PUBLICATIONS

European Search Report for EP09251693 date of completion is Oct. 23, 2009 (3 pages).

\* cited by examiner

SURGICAL STAPLING APPARATUS WITH POWERED RETRACTION

CROSS-REFERENCE TO RELATED APPLICATIONS

This application is a continuation of U.S. patent application Ser. No. 13/913,538, filed Jun. 10, 2013, which is a continuation of U.S. patent application Ser. No. 13/489,517, filed Jun. 6, 2012, (now U.S. Pat. No. 8,479,967), which is a continuation of U.S. patent application Ser. No. 13/196,126, filed Aug. 2, 2011, (now U.S. Pat. No. 8,210,412), which is a continuation of U.S. patent application Ser. No. 11/784,804, filed Apr. 9, 2007, (now U.S. Pat. No. 8,006,885), the entire contents of each of which are incorporated herein by reference.

BACKGROUND

Technical Field

The present disclosure relates to a surgical stapling apparatus. More particularly, the present disclosure relates to an endoscopic surgical stapling apparatus including a mechanism for retracting the actuation shaft of a surgical stapling apparatus.

Background of Related Art

Surgical devices capable of fastening tissue portions are well known in the art. Some of these devices include a knife to cut the tissue that has been joined by the fasteners. Although the fasteners are typically in the form of surgical staples, two-part polymeric fasteners may also be employed.

Surgical fastening instruments can include two elongated jaw members used to capture or clamp tissue. One jaw member typically contains a staple cartridge that houses a plurality of staples arranged in at least two lateral rows while the other jaw member has an anvil that defines a surface for forming the staple legs as the staples are driven from the staple cartridge. The stapling operation is usually effected by cam members that translate through the staple cartridge, with the cam members acting upon staple pushers to sequentially eject the staples from the staple cartridge. A knife may move axially between the staple rows to cut or open the stapled tissue between the rows of staples. U.S. Pat. Nos. 3,079,606 and 3,490,675 disclose examples of this kind of instrument.

A stapling apparatus disclosed in U.S. Pat. No. 3,499,591 also applies a double row of staples on each side of the incision. The patent discloses a surgical stapler having a disposable loading unit wherein a cam member moves through an elongate guide path between two sets of staggered staple carrying grooves. Staple drive members are located within the grooves and are positioned in such a manner so as to be contacted by the longitudinally moving cam member. The staple members eject the staples in the staple cartridge as the cam member moves axially along the elongate guide path. Other examples of such staplers are disclosed in U.S. Pat. Nos. 4,429,695 and 5,065,929.

Each of the instruments described hereinabove is designed for use in conventional surgical procedures wherein surgeons have direct manual access to the operative site. In endoscopic or laparoscopic procedures, however, surgery is performed through a small incision or through a narrow cannula inserted through small entrance wounds in the skin. Endoscopic surgical stapling devices have been developed to address the specific needs of endoscopic and laparoscopic surgical procedures. A few examples of endoscopic surgical stapling devices are disclosed in U.S. Pat. Nos. 5,307,976; 5,312,023; 5,326,013; 5,332,142; and 6,241,139, the entire contents of each of which are incorporated herein by reference.

Tyco Healthcare, LP, the assignee of the present application, has manufactured and marketed endoscopic stapling instruments, such as the ENDO GIA™ Universal and Universal XL instruments, for a number of years. See FIGS. 1-3. These instruments include a surgical stapling apparatus having a retraction mechanism to return surgical stapling apparatus to a retracted position. The retraction mechanism may include a pair of retractor knobs movably positioned along a barrel portion of a handle assembly. After firing staples, the retraction knobs may be manually pulled proximally to retract the actuation shaft of the surgical stapling apparatus to its original position. These instruments have provided significant clinical benefits. Nonetheless, improvements to these instruments are possible.

For instance, it would be extremely beneficial to provide a surgical stapling apparatus allowing a user to quickly and effortlessly retract the actuation shaft of the surgical instrument with one hand. It would also be desirable to provide a surgical stapling apparatus with a compact, simple, reliable and ergonomic powered retraction mechanism. In addition, it would be beneficial to provide a surgical stapling apparatus with a powered retraction mechanism that can be manually overridden.

SUMMARY

The presently disclosed surgical stapling apparatus has a handle assembly, an actuation shaft having a connector, and a retraction mechanism positioned within the handle assembly. The retraction mechanism includes a motor coupled to a transmission shaft, a first gear rotatably mounted on the transmission shaft, the first gear configured to engage a second gear, a clutch operatively attached to the second gear, a main shaft connected to the clutch, and a pulley coupled to the main shaft, the pulley being operatively attached to the connector. The surgical stapling apparatus may further include at least one retraction knob operatively attached to a proximal end of the actuation shaft and configured for manually returning the actuation shaft to the retracted position after firing. The actuation shaft may be attached to the at least one retraction knob via a coupling pin.

A cable may interconnect the proximal end of the connector and the pulley. The cable could be maintained in tension by a spring motor coupled to the pulley. The spring motor includes a spring element wrapped around and interconnecting at least two arbors.

The clutch includes first and second discs. The first disc is rotatably connected to the second gear and the second disc is slidably and rotatably mounted on the main shaft. The clutch may further include a button configured to turn on the motor and engage the clutch.

An operator may use the retraction mechanism to return the actuation shaft of the surgical stapling apparatus to a retracted position by activating the motor and engaging the clutch.

DETAILED DESCRIPTION

The embodiments of the present disclosure will now be described in detail with reference to the drawings, in which like reference numerals designate identical or corresponding elements in each of the several views.

In the drawings and the description that follows, the term "proximal," as is traditional, will refer to the end of the stapling apparatus that is closest to the operator, while the term "distal" will refer to the end of the apparatus that is farthest from the operator.

Figure 1:
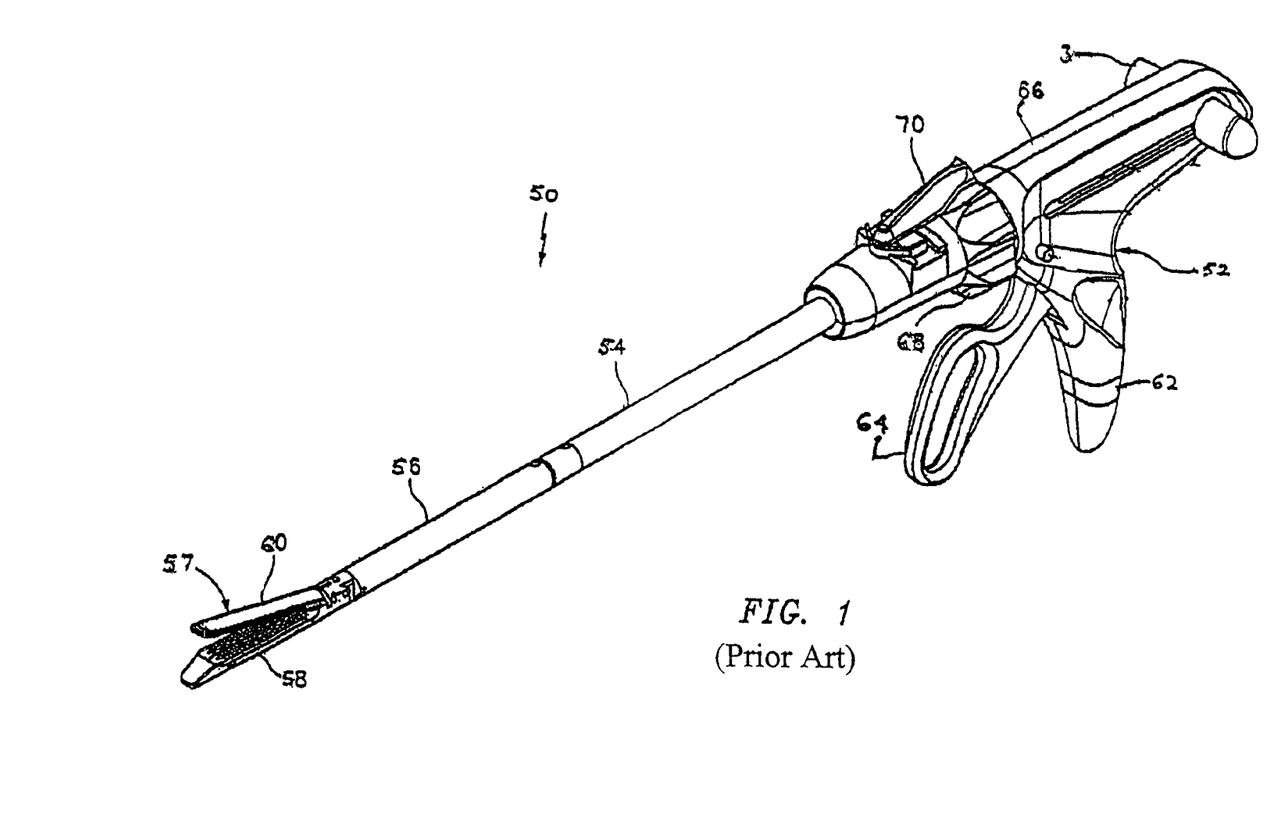
FIGS. 1-3 illustrate a prior art surgical stapler.
Figure 2:
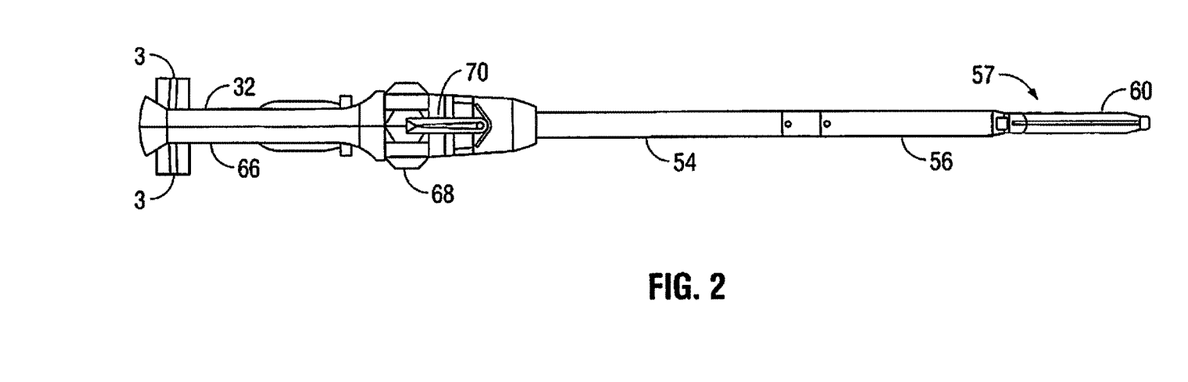
Figure 3:
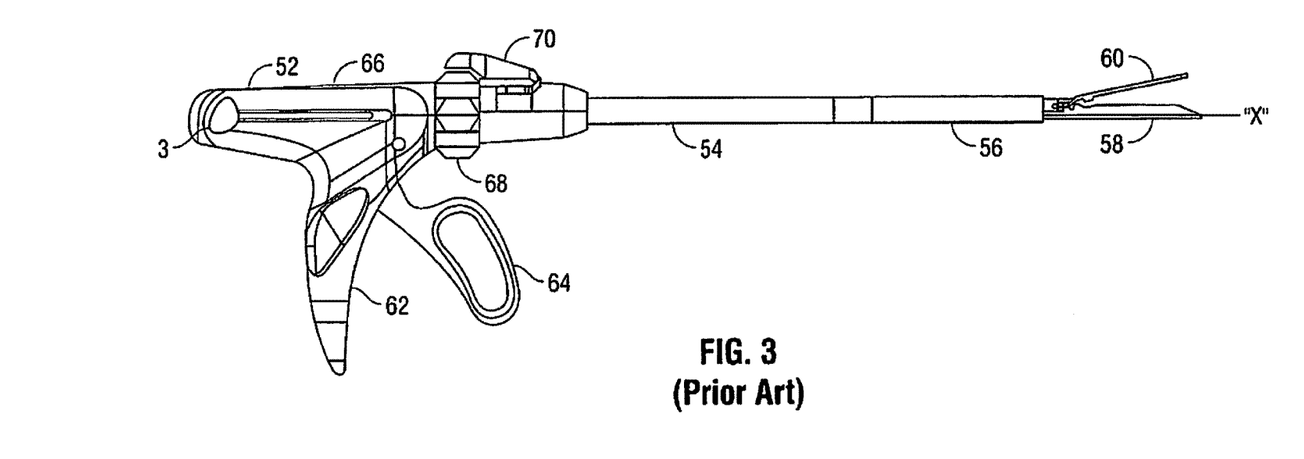

FIGS. 1-3 illustrate a prior art surgical stapling apparatus generally referred as 50. In the interest of brevity, this disclosure will focus primarily on systems, methods and structures for returning an actuation shaft of surgical stapling apparatus 50 to its retracted position. A detailed discussion of the remaining components and method of use of surgical stapling apparatus 50 is disclosed in U.S. Pat. No. 6,953,139, the entire disclosure of which is incorporated herein by reference.

Surgical stapling apparatus 50 is an endoscopic apparatus and includes a handle assembly 52 and an elongated body 54 extending therefrom. A single use loading unit ("SULU") 56 is releasably secured to the distal end of elongated body 54. Although the drawings illustrate a SULU 56, a person having ordinary skill in the art will recognize that other end effector may be used. SULU 56 includes a tool assembly 57 having a cartridge assembly 58 housing a plurality of surgical staples and an anvil assembly 60 movably secured in relation to cartridge assembly 58. As illustrated in FIGS. 1-3, SULU 56 is configured to apply at least one row of staples. SULUs may have various staple line lengths and configurations. Some typical SULUs have staple line lengths measuring from about 30 mm to 60 mm in length. SULUs for applying any number of rows of staples, having staple pockets arranged in various patterns, or end effectors having any other length, are also envisioned. Loading units can include those that provide articulating tool assembly or a tool assembly that does not articulate, as disclosed in U.S. Pat. No. 6,953,139, the disclosure of which is hereby incorporated by reference herein.

Handle assembly 52 includes a stationary handle member 62, a movable handle member 64, and a barrel portion 66 defining a longitudinal axis "X." A rotatable member 68 may be mounted on the distal end of barrel portion 66 to facilitate rotation of elongated body 54 with respect to handle assembly 52. An articulation lever 70 may also be provided at the barrel portion 66 adjacent to rotatable knob 68 to facilitate articulation of tool assembly 57. A pair of retraction knobs 3 are movably positioned along barrel portion 66 to return surgical stapling apparatus 50 to a retracted position, as will be described in detail below.

Figure 4:
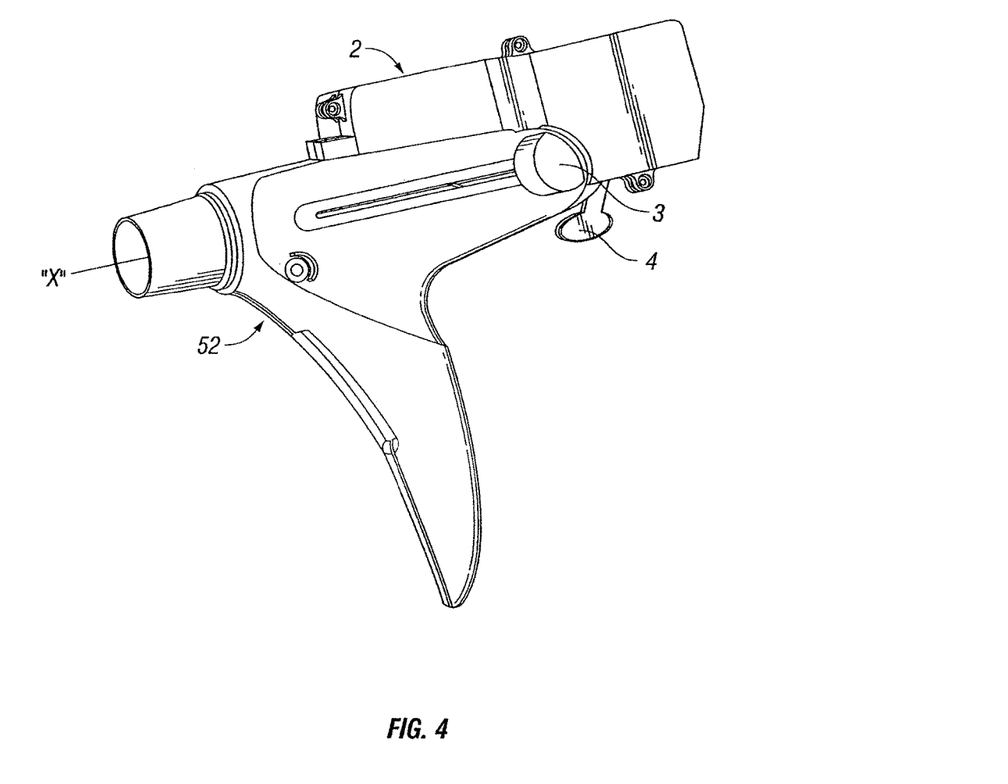
FIG. 4 is a perspective view of the handle assembly according to an embodiment of the presently disclosed surgical stapling apparatus.
Figure 5:
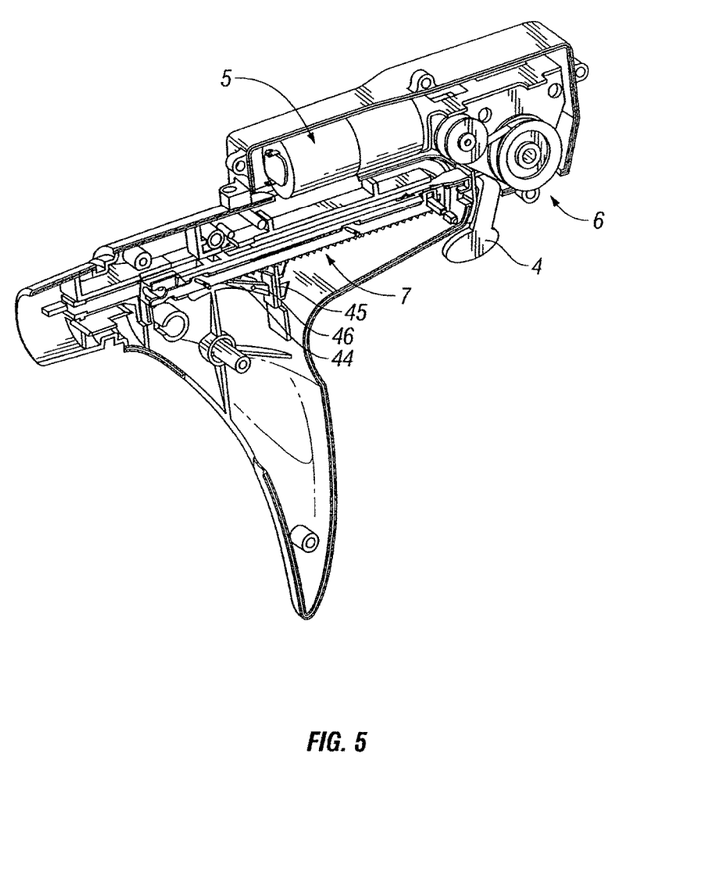
FIG. 5 is a perspective cross-sectional view of the handle assembly shown in FIG. 2.

Referring now to FIGS. 4 and 5, handle assembly 52 includes a retraction mechanism 2 positioned generally along longitudinal axis "X" and a button 4 for activating retraction mechanism 2. Button 4 is dimensioned and positioned so that a user may easily reach it. Retraction mechanism 2 further includes a retraction drive 6 supported within handle assembly 52, and a motor 5 operatively coupled to retraction drive 6. An internal or external battery pack, or a cable connecting the retraction mechanism 2 to an external power source, may be used to energize motor 5.

Figure 6:
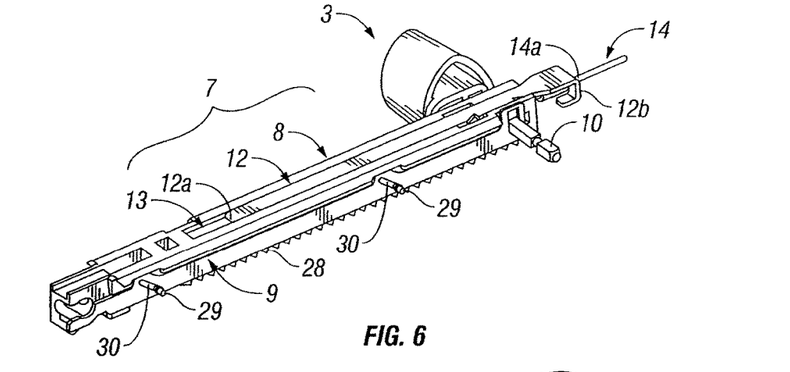
FIG. 6 is a perspective view of a portion of an embodiment of the presently disclosed surgical stapling apparatus.
Figure 7:
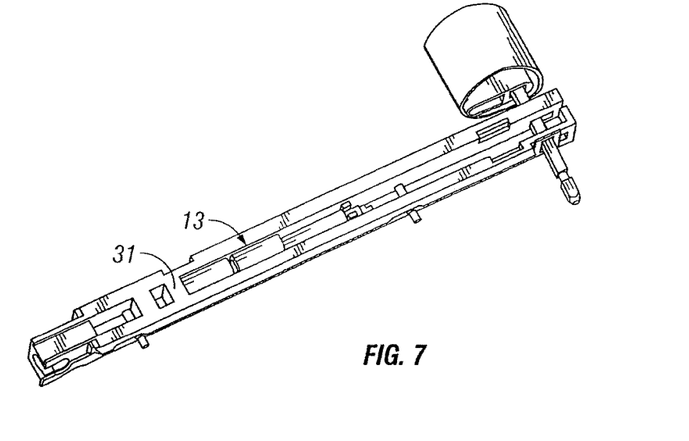
FIG. 7 is a perspective view of a portion of an embodiment of the presently disclosed surgical stapling apparatus.

Referring to FIGS. 6 and 7, rack assembly 7 has an actuation shaft 8 supported within barrel portion 66, and a release plate 9 operatively associated with actuation shaft 8. Actuation shaft 8 has a toothed rack 28 and its proximal end is connected to the pair of retraction knobs 3 via a coupling pin 10. Release plate 9 is configured for movement with respect to actuation shaft 8 in response to manipulation of retraction knobs 3 or activation of retraction mechanism 2. A pair of spaced apart pins 29 extend outwardly from a lateral face of actuation shaft 8 to engage a pair of corresponding angled cam slots 30 formed in released plate 9. Actuation shaft 8 is biased proximally by spring 13. U.S. Pat. No. 7,044,353, the disclosure of which is hereby incorporated by reference herein, describes in detail the structure and manual operation of the rack assembly 7, actuation shaft 8, and release plate 9.

Referring to FIG. 5, handle assembly 52 is provided with a pawl 44 that is mounted to selectively engage toothed rack 28 and advances the actuation shaft 8 in a distal direction in response to manipulation of handle member 64 (see FIG. 2) through an actuating stroke. Pawl 44 is mounted to handle member 64 by a pivot pin 46. The mounting portion of pawl 44 is curved to interact with an abutment wall 45, and the pawl 44 is rotated out of engagement with the toothed rack 28 of actuation shaft 8.

To fire apparatus 50 and apply a plurality of surgical fasteners to a tissue clamped in tool assembly 57, movable handle member 64 is manipulated toward a stationary handle member 62. Thereupon, pawl 44 engages toothed rack 28 and drives actuation shaft 8 distally. The distal advancement of actuation shaft 8 caused by one full stroke of movable handle member 64 will be dictated by the size and configuration of the actuation shaft 8. Actuation shaft 8 may have various sizes and configurations.

To complete the staple firing operation, movable handle member 64 is once again approximated toward stationary handle 24, causing pawl 44 to engage toothed rack 28 and advance actuation shaft 8 in a distal direction another 15 mm. Thus, in one embodiment, two complete strokes of actuation handle 64 may cause actuation shaft 8 to advance 30 mm within barrel portion 66, causing the sequential ejection of all the surgical fasteners in staple cartridge 58. If desired, the operator can incrementally advance actuation shaft 8 by multiple short strokes, wherein the minimum advancement is dictated by the linear distance between the teeth on rack 28. Therefore, while two complete strokes of a stroke distance of 15 mm can be used (to fire a 30 mm disposable loading unit), complete strokes are not necessary or required. Surgical stapling apparatus 50 may be configured to have various stroke distances.

Figure 8:
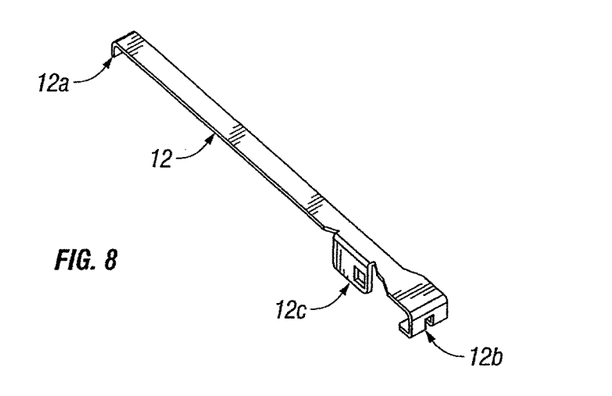
FIG. 8 is perspective view of a connector of an embodiment of the presently disclosed surgical stapling apparatus.
Figure 9:
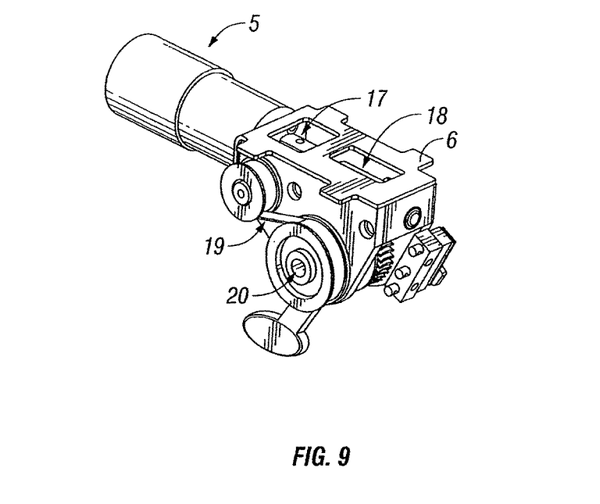
FIG. 9 is a perspective view of a portion of the retraction mechanism of an embodiment of the presently disclosed surgical stapling apparatus.
Figure 12:
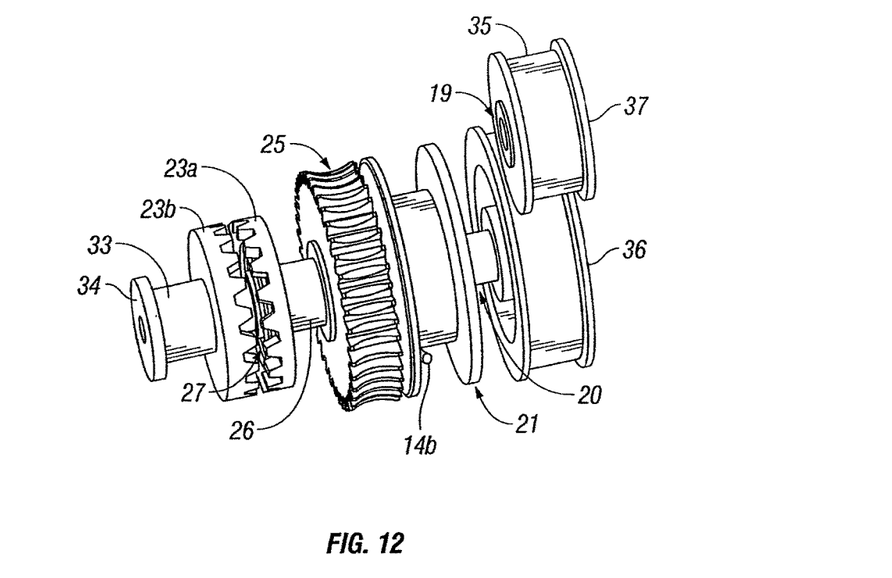
FIG. 12 is a perspective view of a portion of the retraction mechanism of an embodiment of the presently disclosed surgical stapling apparatus.

With reference to FIGS. 6-8, to enable powered retraction, rack assembly 7 may include a distally biased connector 12 having distal and proximal ends 12a, 12b. A biasing block 13, which is positioned adjacent to proximal end 12a, biases connecter 12 distally. Connector 12 is mounted on a top portion of rack assembly 7 and has a hole 12c dimensioned and configured for receiving coupling pin 10. The distal end 14a of a cable 14 is attached to the proximal end 12b of connector 12. The proximal end 14b of cable 14 is attached to a pulley 21 of retraction drive 6, as seen in FIG. 12.

Referring to FIGS. 9-12, retraction drive 6 includes a transmission shaft 17 operatively connected to motor 5. A coupling 38 (FIG. 11) interconnects motor 5 and transmission shaft 17. A first gear 18 is rigidly mounted to transmission shaft 17 and configured to engage a second gear 25. First and second gears 18, 25 effectively reduce the speed of the rotational motion supplied by motor 5. One skilled in the art will recognize that other speed reducing means may be utilized in lieu of first and second gears 18, 25. Second gear 25 is connected to hollow shaft 26. Hollow shaft 26, in turn, is operatively coupled to a first disc 23a of a slip clutch 23. Slip clutch 23 is biased to its open position and has a second disc 23b slidably and rotatably mounted on a main shaft 20. Second disc 23b may include a tubular portion 33 having a flange 34 attached thereto. Tubular portion 33 may surrounds at least a portion of main shaft 20.

Main shaft 20 is partially surrounded by hollow shaft 26 and is connected to pulley 21. Additionally, main shaft 20 interconnects pulley 21 and spring motor 19. Spring motor 19 may include a spring element 35 wrapped around and interconnecting first and second arbors 36, 37. Further, spring motor 19 may be configured to maintain cable 14 in tension, thereby preventing its entanglement.

Figure 10:
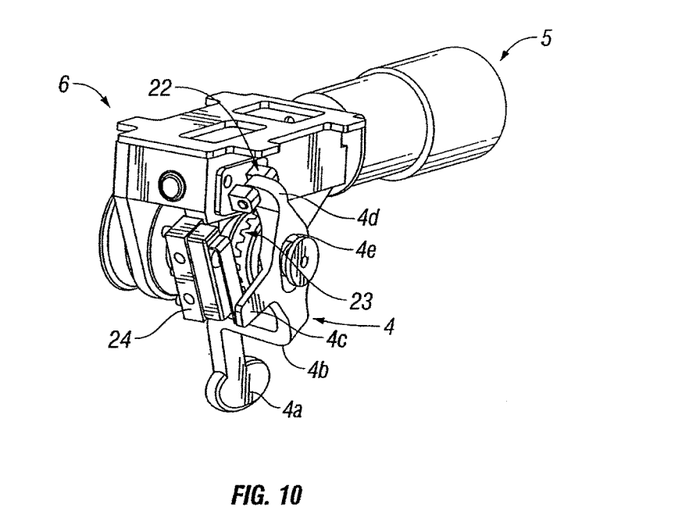
FIG. 10 is a perspective view of a portion of the retraction mechanism of an embodiment of the presently disclosed surgical stapling apparatus.

With specific reference to FIG. 10, retraction drive 6 includes a button 4 configured to turn on motor 5 and engage clutch 23. Button 4 may have a bottom portion 4a, an elongated body portion 4b, a protrusion 4c configured to engage a switch 24, a hole 4e sized for receiving a tubular portion 33 of second disc 23b, and an upper portion 4d pivotably coupled to a joint 22 of retraction drive 6. A switch 24 is positioned adjacent to protrusion 4c of button 4 and controls the electrical conduction between a motor 5 and the selected power source.

Figure 10A:
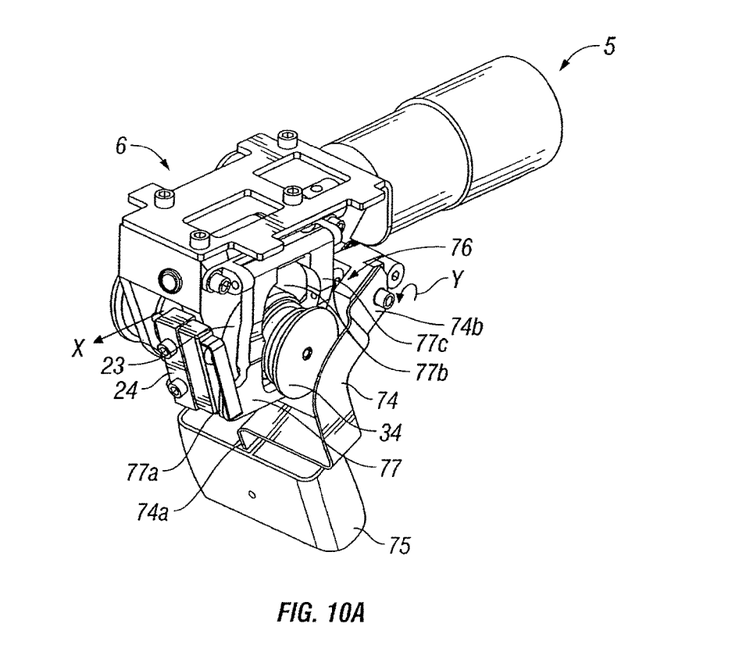
FIG. 10a is a perspective view of a portion of the retraction mechanism of an embodiment of the presently disclosed surgical stapling apparatus.
Figure 10B:
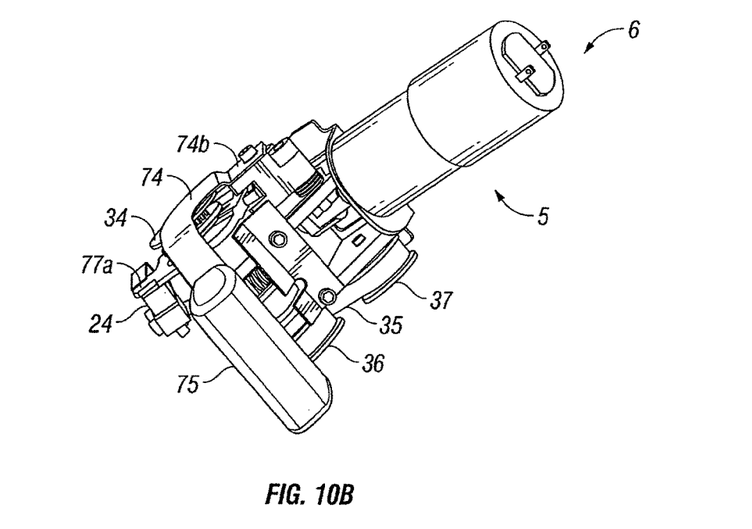
FIG. 10b is a perspective view of a portion of the retraction mechanism of an embodiment of the presently disclosed surgical stapling apparatus.
Figure 11:
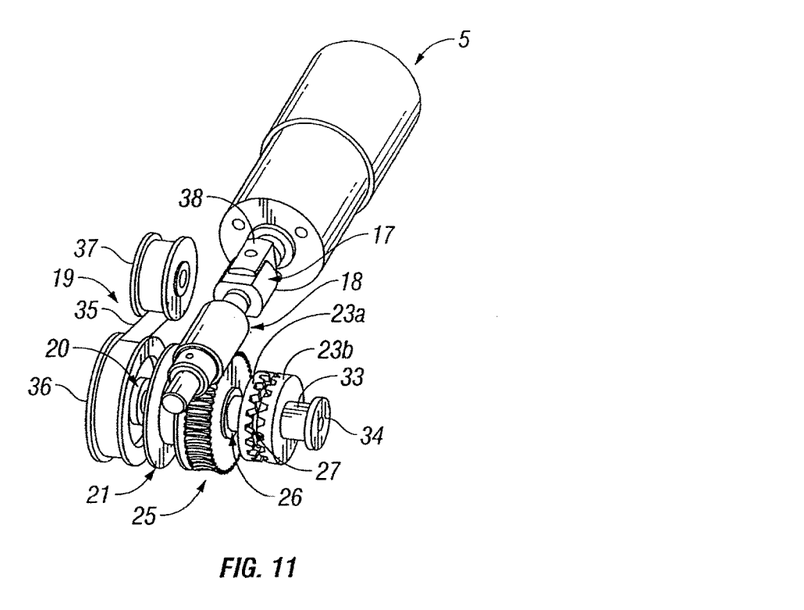
FIG. 11 is a perspective view of a portion of the retraction mechanism of an embodiment of the presently disclosed surgical stapling apparatus.

With reference to FIGS. 10a and 10b, an alternative embodiment of retraction drive 6 includes an activation lever 74 adapted to activate on motor 5. Activation lever 74 has a lower portion 74a and an upper portion 74b. Lower portion 74a is connected to an actuation structure 75. A user can manipulate activation lever 74 through actuation structure 75. Activation lever 74 acts along the major plane of the apparatus 50 to allow ergonomical activation. The upper portion 74b of activation lever 74 is coupled to a cam 76. A lever 77 is operatively connected to cam 76 and pivotably coupled to an upper portion of retraction drive 6. Specifically, lever 77 includes a protrusion 77a configured to manipulate switch 24, an opening 77b dimensioned to receive tubular portion 33 (see FIG. 11), and at least one column 77c configured to engage clutch 23. Switch 24 is connected to protrusion 77a of lever 77 and controls the electrical conduction between a motor 5 and the selected power source. Cam 76 translates the rotation of activation lever 74 with respect to a longitudinal axis "Y" into rotation of lever 77 with respect to longitudinal axis "X."

In operation, a user fires a staple or any other surgical fastener using surgical stapling apparatus 50, as discussed in detail in U.S. Pat. No. 7,044,353, the disclosure of which is hereby incorporated by reference herein, by operating movable handle member 64 to advance actuation shaft 8. Thereafter, an operator may automatically return actuation shaft 8 to its retracted position by employing retraction mechanism 2.

To activate retraction mechanism 2, a user must press button 4 to turn on motor 5 and engage clutch 23 when operating the embodiment depicted in FIG. 10. Specifically, as a surgeon activates retraction mechanism 2, button 4 pivots about joint 22 and slides disc 23b towards disc 23a, thus engaging clutch 23. In addition, switch 24 allows electrical connection between a power source and motor 5, thereby energizing motor 5.

In the embodiment illustrated in FIGS. 10a and 10b, a user can move activation structure 75 to manipulate activation lever 77, thereby turning on motor 5 and engaging clutch 23. Specifically, as a user moves activation structure 75, activation lever 74 rotates with respect to longitudinal axis "Y." Cam 76 transforms the rotational motion of lever 74 into a rotational motion of lever 77 with respect to longitudinal axis "X." Thereafter, lever 77 engages clutch 23 and manipulates switch 24 to activate motor 5.

When motor 5 rotates transmission shaft 17, first gear 18 rotates and causes the corresponding rotation of second gear 25. The interaction of first and second gears 18, 25 reduces the rotation speed produced by motor 5. Clutch 23 transfers the rotational motion of second gear 25 to main shaft 20 and, consequently, to pulley 21. As pulley 21 rotates, it pulls back actuation shaft 8 through cable 14. Upon deactivation of button 4, clutch 23 returns to its open position, and motor 5 is turned off. Alternatively, actuation shaft 8 may be manually returned to its retracted position by pulling retraction knobs 3 proximally. The clutch 23, which is biased to its open position, enables the manual retraction of the actuation shaft 8, without engaging the motor 5. The release plate 9 removes the pawl from engagement with the actuation shaft 8 so that the actuation shaft can be retracted either manually or through the motor without interfering with handle 64.

The user of the surgical stapling apparatus 50 can operate the movable handle member 64 to fire the apparatus 50 and then use the same hand to actuate powered retraction of the actuation shaft 8. After retraction, the used loading unit 56 may be replaced with another loading unit of the same or different configuration and staples can again be fired using the apparatus 50.

In further embodiments, the firing movement and retraction of an actuation shaft can be actuated through other mechanisms. For example, the retraction mechanism 2 discussed above can be used to retract an actuation shaft that has been driven forwards through a movable handle and gear mechanism, a motor driven mechanism or other powered or manual actuation.

It will be understood that various modifications may be made to the embodiments disclosed herein. Therefore, the above description should not be construed as limiting, but merely exemplifications of embodiments. For instance, the described surgical stapling apparatus 50 may be use in combination with a servomotor, position sensor, slide ring, electric brakes and electronic controls to add functions such as controlling retraction speed, sensing the limits with automatic stop, etc. Those skilled in the art will envision other modification within the scope and spirit of the claims appended thereto.

What is claimed is:

1. A surgical device, comprising:
   a tool assembly;
   an actuation shaft moveable in a first direction to effect a function of the tool assembly; and
   a retraction mechanism including:
      a clutch including first and second discs, at least one of the first or second discs movable between a disengaged state in which the first and second discs are spaced apart from one another and an engaged state in which the first and second discs are engaged with one another for concomitant rotation, the second disc operatively coupled to the actuation shaft, wherein when the first and second discs are in the engaged state:
         rotation of the second disc, in a first direction, causes translation of the actuation shaft in a second direction; and
         rotation of the second disc, in a second direction opposite to the first direction, results in no translation of the actuation shaft.

2. The surgical device according to claim 1, wherein the clutch is biased toward the disengaged state.

3. The surgical device according to claim 1, wherein the retraction mechanism further includes a hollow shaft having the first disc mounted thereon and a main shaft having the second disc slidably mounted thereon, wherein a portion of the main shaft is disposed within the hollow shaft.

4. The surgical device according to claim 3, wherein the retraction mechanism further includes a first gear coupled to a motor and a second gear mounted on the hollow shaft, the first and second gears configured to reduce the speed of a rotational output of the motor.

5. The surgical device according to claim 1, wherein the retraction mechanism further includes a pulley operatively coupled to the actuation shaft.

6. The surgical device according to claim 5, wherein the retraction mechanism further includes a cable interconnecting the actuation shaft and the pulley.

7. The surgical device according to claim 6, wherein the retraction mechanism further includes a spring motor coupled to the pulley to maintain the cable in tension.

8. The surgical device according to claim 1, further comprising a motor operatively coupled to the first disc, wherein the motor is actuated when the clutch is in the engaged state.

9. The surgical device according to claim 8, wherein the retraction mechanism further includes a power source to supply electric power to the motor.

10. The surgical device according to claim 1, wherein the retraction mechanism further includes a knob coupled to the actuation shaft for manual repositioning of the actuation shaft.

11. The surgical device according to claim 1, wherein the retraction mechanism further includes an actuation button to transition the clutch between the engaged and disengaged states.

12. A method of surgery, comprising:
    providing a surgical device including:
       a tool assembly;
       an actuation shaft operatively coupled with the tool assembly; and
       a retraction mechanism including:
          a clutch including first and second discs, the clutch transitionable between a disengaged state in which the first and second discs are spaced apart from one another and an engaged state in which the first and second discs are engaged with one another for concomitant rotation, the second disc operatively coupled to the actuation shaft;
    advancing the actuation shaft in a first direction to effect a function of the tool assembly; and
    advancing the actuation shaft in a second direction to a retracted position.

13. The method according to claim 12, wherein advancing the actuation shaft in the second direction includes rotating the second disc while in the engaged state.

14. The method according to claim 13, wherein rotating the second disc in the engaged state includes actuating a motor operatively coupled to the first disc.

15. The method according to claim 12, wherein advancing the actuation shaft in the first direction to effect the function of the tool assembly includes firing surgical fasteners from the tool assembly.

16. The method according to claim 12, wherein advancing the actuation shaft in the second direction includes transitioning the clutch from the disengaged state to the engaged state.

17. The method according to claim 16, wherein transitioning the clutch from the disengaged state to the engaged state includes moving the first disc mounted on a hollow shaft toward the second disc slidably mounted on a main shaft disposed within the hollow shaft.

\* \* \* \* \*